United States Patent [19]

Lin et al.

[11] Patent Number: 4,983,513
[45] Date of Patent: Jan. 8, 1991

[54] SULFHYDRYL COMPOUNDS FOR SUPPRESSING THE INHIBITORY EFFECTS OF NAD DEGRADATION PRODUCTS ON LD-L ACTIVITY

[75] Inventors: Tsung-I Lin, Yorba Linda; Alice C. Liu, Westminster, both of Calif.

[73] Assignee: Beckman Instruments, Inc., Fullerton, Calif.

[21] Appl. No.: 845,883

[22] Filed: Mar. 28, 1986

[51] Int. Cl.$^5$ .............................. C12Q 1/32
[52] U.S. Cl. .......................... 435/26; 435/4; 435/25; 435/176
[58] Field of Search ................ 435/4, 25, 26; 436/176

[56] References Cited

U.S. PATENT DOCUMENTS

| | | |
|---|---|---|
| 3,746,625 | 7/1973 | Bergmeyer et al. |
| 4,067,775 | 1/1978 | Wurzburg et al. |
| 4,229,369 | 10/1980 | Green |
| 4,277,562 | 7/1981 | Modrovich ............ 435/26 |
| 4,372,874 | 2/1983 | Modrovich ............ 435/17 |

OTHER PUBLICATIONS

Beckman Astra$_{TM}$ System LD-L Kit Brochure, 1984.
Beckman Liquid-Stat$_{TM}$ Liquid Enzyme Reagent Brochure, 1979.
Calbiochem-Behring Stat-Pack$_{TM}$ Ethyl Alcohol Test Brochure, 1983.
Kaplan et al., Effect of Alkali on Disphosphopyridine Nucleotide (1951), J. Biol. Chem., vol. 191, pp. 461–472.
Dalziel, The Purification of Nicotinamide Adenine Dinucleotide and the Kinetic Effects of Nucleotide Impurities (1963); J. Biol. Chem., vol. 238, pp. 1538–1543.
Dagaiczyk et al., The Effect of Cystein on L—Glycerophosphate and Lactate Dehydrogenase Reactions (1968), J. Biol. Chem., vol. 243, pp. 2236–2240.
Klotzch et al., Inhibitor-Contaminated NADH: Its Influence on Dehydrogenases and Dehydrogenase-Coupled Reactions (1969), Clin. Chem., vol. 15; p. 1056–1061.
Babson et al., Lactic Dehydrogenase Inhibitors in NAD (1970), Clin. Chem., vol. 16, 0. 254–255.
Guilbert et al., Investigation of the Open Ring Form of Nicotinamide Adenine Dinucleotide (1977), Biochemistry, vol. 16, pp. 355–344.
Margolis et al., Base-Catalyzed Rearrangement of NAD (1978), Fed. Proc., vol. 37, p. 1347.

*Primary Examiner*—Sam Rosen
*Attorney, Agent, or Firm*—Danton K. Mak

[57] ABSTRACT

A liquid coenzyme reagent comprises the coenzyme nicotinamide adenine dinucleotide (NAD), or nicotinamide adenine dinucleotide phosphate (NADP), and a sulfhydryl compound capable of counteracting the inhibitory effects of NAD (or NADP) degradation products on LD-L activity. The reagent is maintained at a pH of less than about 3½. The liquid reagent has a shelf life of at least about 2 years, maintaining a LD-L activity of at least 90% that of the reagent when fresh, when stored at a temperature of from 2°–8° C.

57 Claims, 9 Drawing Sheets

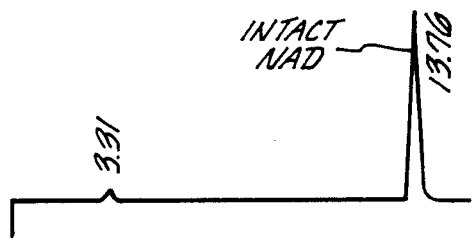
FIG_1.
HPLC CHROMATOGRAPH
OF FRESH NAD REAGENT
| TIME | CONC. |
|---|---|
| 3:31 | 4.8841 |
| 13.76 | 95.1158 |
| TOTAL | 100 |
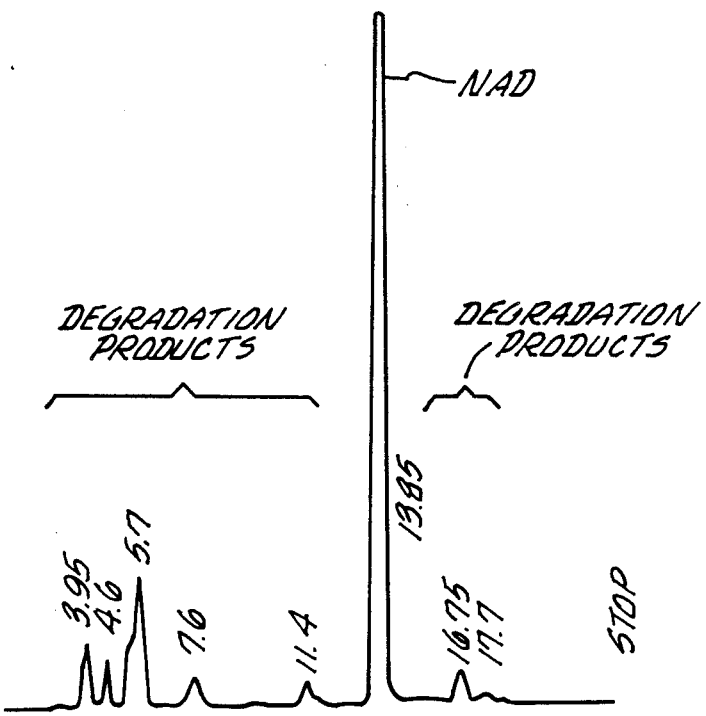
FIG_2.
HPLC CHROMATOGRAPH
OF NAD
REAGENT STORED A 4°C
FOR ABOUT 1 YEAR.
| TIME | CONC. |
|---|---|
| 3.95 | 3.9988 |
| 4.6 | 2.2219 |
| 5.7 | 11.9004 |
| 7.6 | 3.1448 |
| 11.4 | 2.1574 |
| 13.85 | 72.5196 |
| 16.75 | 3.5302 |
| 17.7 | 0.5264 |
| TOTAL | 100 |

| TIME | CONC. |
|---|---|
| 2.88 | 0.6077 |
| 3.93 | 10.5419 |
| 4.63 | 6.1721 |
| 5.43 | 23.3543 |
| 7.23 | 3.5412 |
| 9.03 | 0.5810 |
| 11.33 | 1.3364 |
| 13.93 | 44.2165 |
| 16.68 | 7.6955 |
| 17.53 | 1.9524 |
| TOTAL | 99.9999 |

HPLC CHROMATOGRAPH OF FRESH NAD REAGENT STRESSED AT 41°C FOR 11 DAYS.

HPLC CHROMATOGRAPH OF FRESH NAD REAGENT CONTAINING 170 nM NAC AND STRESSED AT 41°C FOR 11 DAYS.

DECAY OF LD-L ACTIVITY IN NAD REAGENT STRESSED AT 25°C.

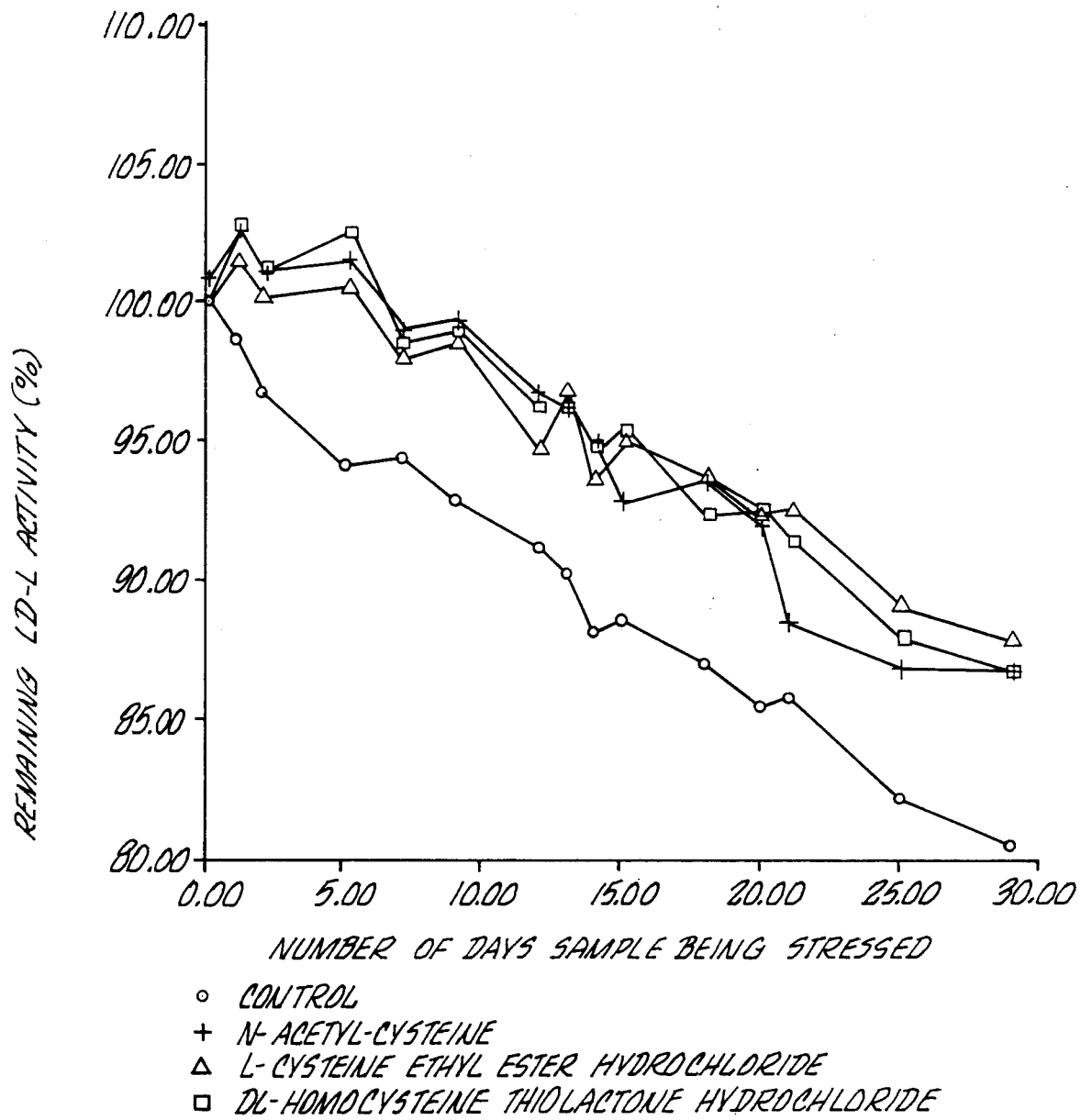

DECAY OF LD-L ACTIVITY IN NAD REAGENT STRESSED AT 37°C

DECAY OF LD-L ACTIVITY IN NAD REAGENTS STRESSED AT 41°C

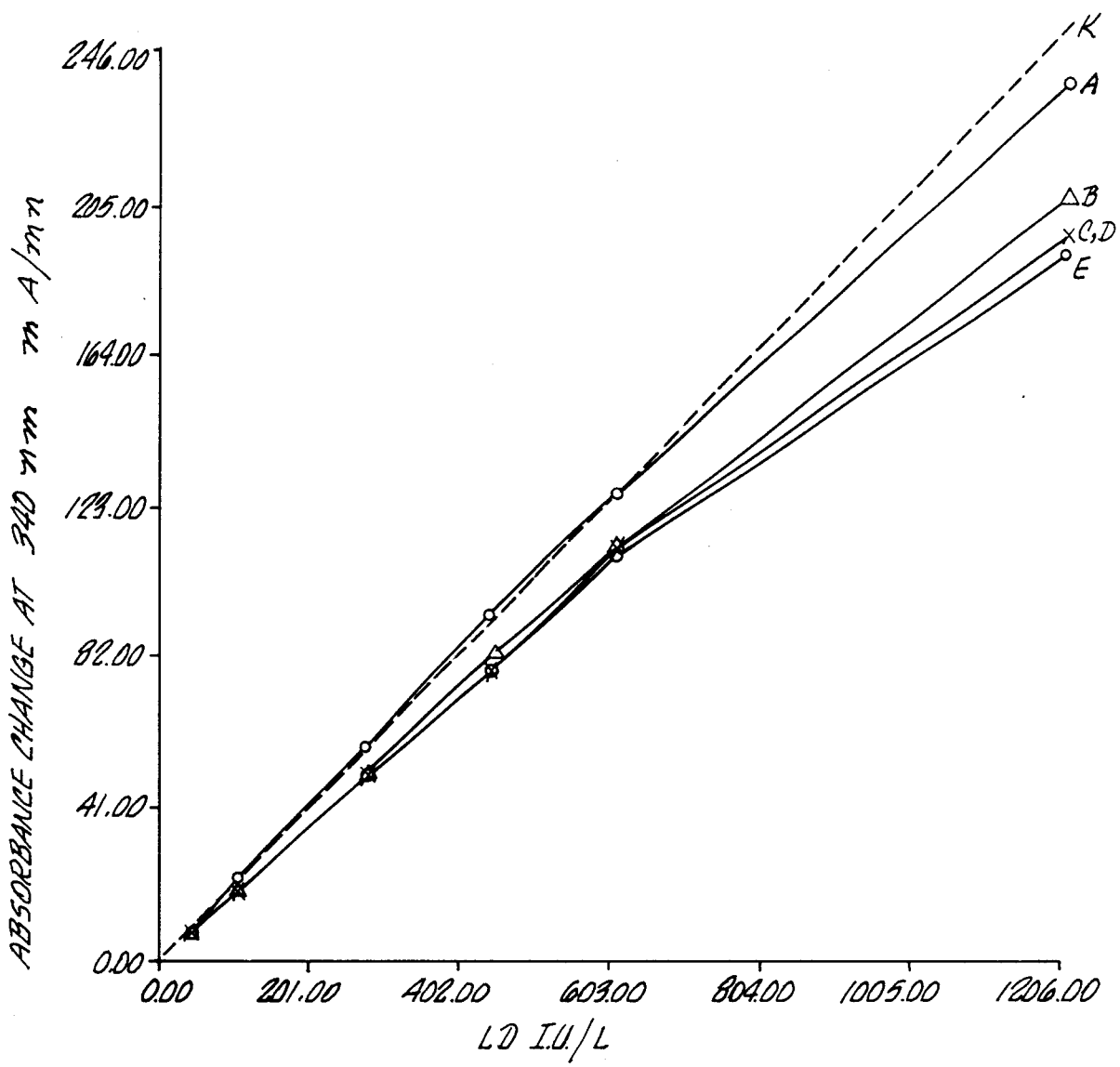
R: DASHED LINE, LINEAR FIT LINE FOR THE CONTROL
A: CONTROL UNSTRESSED NAD REAGENT
B: NAD STRESSED 37°C - 8 DAYS
C: NAD+CEE STRESSED 41°C - 8 DAYS
D: NAD+NAC STRESSED 41°C - 8 DAYS
E: NAD+HCTL STRESSED 41°C - 8 DAYS
FIG. 9. LINEARITY OF LD-L CHEMISTRY WITH SULFHYDRYL COMPOUND ADDED.

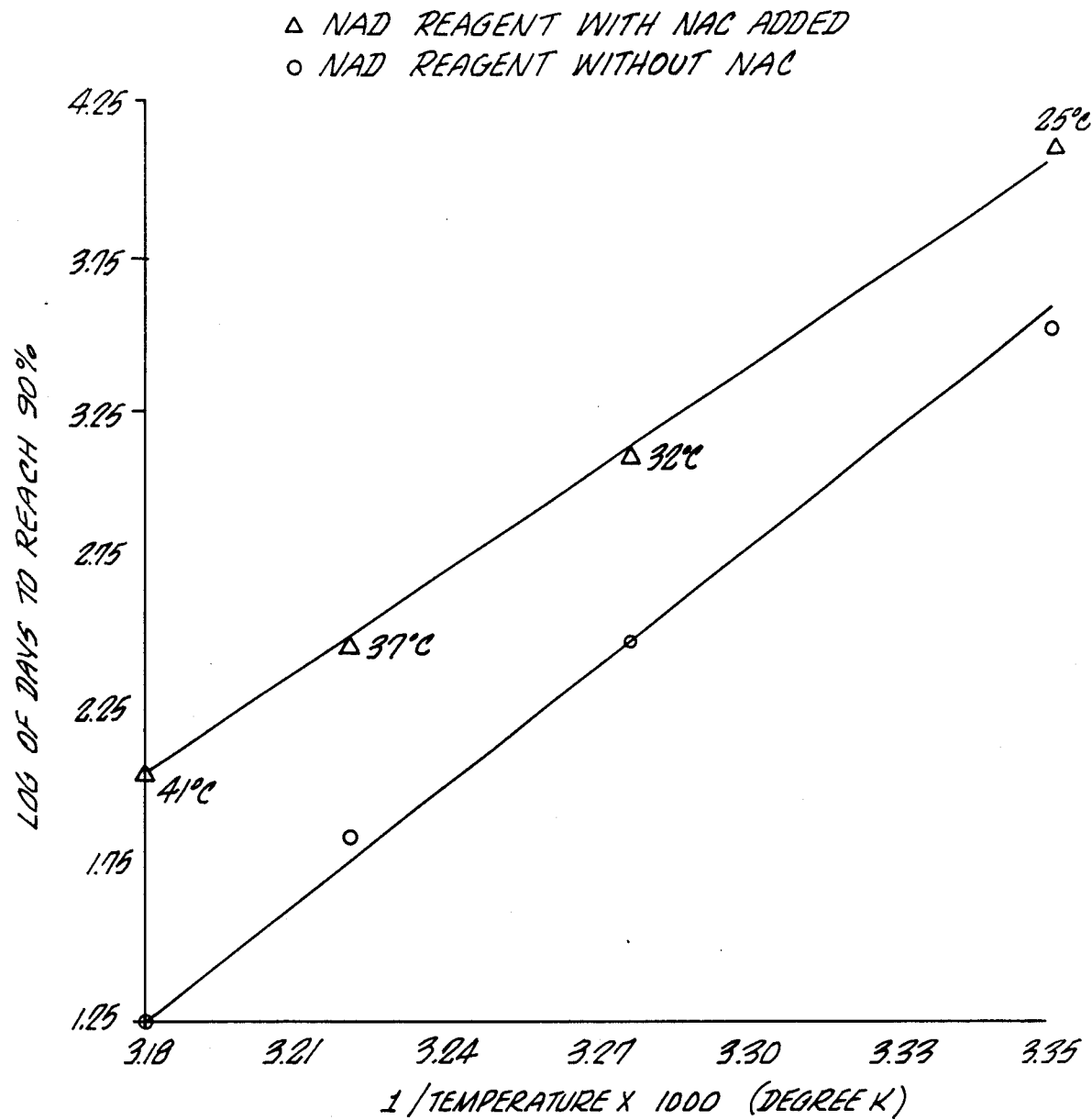
Fig. 10 ARRHENIUS PLOT FOR NAD REAGENTS TO REACH 90% LD-L ACTIVITY.

SULFHYDRYL COMPOUNDS FOR SUPPRESSING THE INHIBITORY EFFECTS OF NAD DEGRADATION PRODUCTS ON LD-L ACTIVITY

BACKGROUND

This invention relates to the use of the coenzyme nicotinamide adenine dinucleotide (NAD) or nicotinamide adenine dinucleotide phosphate (NADP), in a lactate dehydrogenase-lactate assay analytical procedure.

In the determination of enzymes and other biological constitutents, the reaction generally involve enzymes, coenzymes and substrates.

Enzymes are complex proteins with large molecular weights, and are usually of unknown chemical structure. They are classified by their substrate specificity, and catalytic activity. Enzymes are biological catalysts, which can catalyze the reaction of a single substrate, or the reaction of a group of similar substrates.

Coenzymes are organic chemicals with well-defined chemical structures. They usually have lower molecular weights then enzymes. They are required for specific enzyme assay or reaction. Coenzymes are irreversibly changed in their structure and/or atomic composition in the assay. Their reactions are stoichiometric with the substrate. With certain coenzymes having strong absorbance, the creation or disappearance of the absorbing form can be followed photometrically. For example, nicotinamide adenine dinucleotide (NAD) and reduced nicotinamide adenine dinucleotide (NADH) are used in many important clinical assays. Both species have a molecular weight of about 700. NADH absorbs strongly at 340 nm, while NAD does not.

Substrates are organic chemicals of known structure, whose reactions or interactions are catalyzed by enzymes resulting in a change in the substrate's chemical structure, atomic composition, or stereochemistry. In general, substrates are prone to degradation, both chemically and microbiologically. Substrates chemically degrade or hydrolyze in aqueous media, and serve for food for bacteria, fungi and other microorganisms. Typical substrates are glucose, lactate or lactic acid, gluconate and the like.

Because of their high specificity, the use of enzyme determinations has significantly increased during the recent years. At present, the greatest limitation on the use of enzyme reagents lies in the unstable nature of the species therein. Numerous labile components are usually involved. To complicate matters, the exact nature of enzymes, as well as the mechanisms of their action, remains unknown for the most part. Therefore, rigorous quality control measures are required to assure accurate and consistent results. Such measures can be costly.

In the prior art, to ensure strict quality control, emphasis was placed on attempts in stabilizing the labile ingredients in the reagents, i.e., to prevent them for degrading. For example, the enzyme or coenzyme is locked into a solid matrix, either by dry blending, freeze drying, or by locking the chemical structure of the enzyme on to a solid matrix. These methods are expensive, require complicated manufacturing processes, and are less convenient for the user. Product uniformity is difficult to maintain with solid reagents. It was reported that most commercial freeze dried reference serums list an acceptable bottle-to-bottle variation of enzyme constituents at ±10% of the mean. More importantly, the user has to bear the burden of assuring the quality control in the dilution and use of the reagent.

LD-L Chemistry

Although the discussions herein are directed to nicotinamide adenine dinucleotide (NAD), the discussion apply equally well to nicotinamide adenine dinucleotide phosphate (NADP). Lactate dehydrogenase (LD) catalyzes the reversible reaction of lactate (or lactic acid) with the coenzyme nicotinamide adenine dinucleotide (NAD) to form pyruvate and nictotinamide adenine dinucleotide, reduced (NADH).

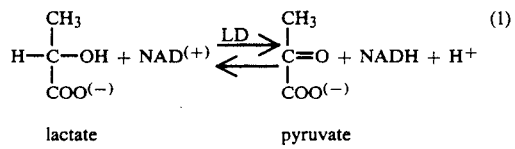

$$\underset{\text{lactate}}{\overset{CH_3}{\underset{COO^{(-)}}{H-C-OH}}} + NAD^{(+)} \overset{LD}{\underset{\longleftarrow}{\longrightarrow}} \underset{\text{pyruvate}}{\overset{CH_3}{\underset{COO^{(-)}}{C=O}}} + NADH + H^+ \quad (1)$$

The above reaction is used extensively in clinical essays, as elevated LD activity has been shown to be associated with many pathological conditions. The above catalyzed reaction is reversible and the reaction rate can be determined in either direction. Therefore the reaction can be used to quantitate any of the species involved: lactate, pyruvate, NAD, NADH, and/or LD. Thus in the case where NADP is the coenzyme, the quantity of lactate, pyruvate, LD, NADP and/or NADPH can be determined.

In the quantitative determination of LD, the procedure of choice is the lactate to pyruvate route, because of greater reaction linearity, better proportionality to LD enzyme present, and better reagent stability. For example, it is known that the degradation products of the reduced coenzyme NADH can contain potent dehydrogenase inhibitors. Also, although the kinetics of the forward reaction are slower, the reverse reaction requires a longer incubation period (10 to 20 minutes, versus about 3 minutes for the forward reaction) after adding NADH and before adding pyruvate, in order to exhaust endogenous substrates in serum. Enzymes activity is generally measured in terms of International Units (IU). One International Unit is defined as the amount of enzyme which will catalyze the conversion of one micromole of substrate per minute under specified conditions. Under LD assay conditions, both the primary substrate (lactate or lactic acid) and the oxidized coenzyme (NAD) are added in excess so that the reaction is limited only by the amount of LD present. As the dehydrogenation reaction proceeds, the increase in absorbance ($\Delta A$) due to the formation of NADH is followed at 340 nm with a spectrophotometer. The $\Delta A$ per unit time can be related directly to micromoles of substrate consumed per unit time, and thus the LD-L activity.

Because of the quality control problems with solid NAD reagents, and because of the convenience factor, users generally prefer liquid, ready-to-use reagents over solid (e.g. lyophilized) compositions. Because of the labile nature of the ingredients involved in LD-L activity determination, generally components of the determinative reagents are stored separately, and are mixed only shortly before the assay is performed.

For example, a liquid reagent system for LD determination can contain a liquid NAD reagent, and a substrate(lactate)/buffer solution. The two are mixed and preincubated shortly before use in the assay. The serum sample which LD concentration is to be determined is then added to the combined reagent, and the rate of change in absorbance (ΔA) over time is measured.

NAD Reagent Stabilization and LD-Inhibition

It is known that liquid NAD reagents degrade over time, especially at elevated temperatures. Therefore NAD reagents are usually stored at a temperature of about 2°-8° C.

Babson et al. reported that NAD preparations can also contain LD-inhibitors. *Lactic Dehydrogenase Inhibitors in NAD*, 254 Clinical Chemistry, vol. 16, No. 3, 1970. LD-inhibitors in NAD can be a serious problem in kinetic determinations, because of the relative large amounts of expensive NAD used (in comparison to colorimetric methods).

It has been suggested in the prior art that NAD can be stabilized in an aqueous medium, i.e., prevented from degrading, by adding a high concentration (35–60 v/v) of an aqueous miscible polyol organic solvent (such as glycerol). It has been suggested that stabilization occurs by protection of the NAD coenzyme from microbial contamination and degradation. The prior art also teaches using a large excess of NAD in the reagent, so that there is always an excess of NAD available, even after substantial degradation of the coenzyme.

For example, an enzyme reagent kit for the quantitative determination of serum LD can comprise a two reagent system, being a substrate-buffer reagent and a coenzyme reagent. The lactate-buffer solution can be an aqueous solution having a typical formulation of sodium lactate, 52 mM; TAPS buffer (tris-(hydroxymethyl) methylamine propane sulfonic acid), 100 mM; preservatives and stabilizers; and a pH of about 8.9. For example the NAD coenzyme reagent can be dissolved in a solvent comprising at least 40% (v/v) of a non-reactive aqueous component, and containing 45–60 (v/v) of an aqueous miscible polyol organic solvent therein. The NAD concentration in the NAD reagent is at least about 50 mM, and preferably is from about 200 to about 400 mM. For example, the NAD coenzyme reagent can contain NAD dissolved in 53% (v/v) glycerol in water, with an NAD concentration of about 327 mM, and a pH of about 1.7 to 2.0. Appropriate volumes of the two reagents are mixed in order to give final concentrations in the mixed reagent of: lactic acid, 50 mM; TAPS buffer, 97 mM; and NAD, 11 mM. The minimum concentration of NAD in the mixed reagent is about 5 mM for an effective assay.

However, it was found that liquid NAD reagents (aqueous solutions), even those having a high organic polyol concentration in the solvent and stored at the recommended temperature range of 2°-8° C., degrade over time. Therefore, even if organic polyol solvent does have any stabilizing effect, the degree of stabilization is still not acceptable. The degradation is demonstrated by the loss of LD-L activity in assays using the aged NAD reagent, and a measurable decrease in the amount of available NAD in the reagent. It is known that NAD degradation increases rapidly at elevated temperatures.

HPLC (high performance liquid chromatograph) studies of aged NAD reagents show that degradation products are formed. It was found that the amount of NAD in the aged reagent, though reduced by degradation, is usually in excess of what is necessary to give full LD-L activity. Yet the LD-L activity of the NAD reagent decays as the reagent ages (such as by extended storage, or when the reagent is subject to thermal stress). The degradation products of NAD actually inhibit LD-L activity. This finding is further supported by the fact that use of larger volumes of the aged NAD solution in the assay mixture further depresses LD-L activity, despite the larger amount of NAD available.

The loss of LD-L activity shows up as lot-to-lot variations, especially with reagents stored for different periods of time. The variation can adversely affect the reliability of LD-L assays. In general, activity variations of up to 10% are deemed acceptable. That is, an aged NAD reagent must at least give 90% of the LD-L activity given by a freshly prepared NAD reagent having an equal amount of NAD to begin with. An aged NAD reagent giving lower than 90% LD-L activity is generally rejected. Currently, NAD reagents with a shelf life of up to about 1 year (2°-8° C. storage) are available.

What is needed is a liquid NAD (or NADP) coenzyme reagent for LD-L determination, with an extended shelf life, e.g. one with a LD-L activity of at least 90% (using a freshly prepared NAD (or NADP) reagent as reference; 100%) for a period of at least two years. What is needed is also a method for rejuvenating the lost activity of an aged liquid NAD or NADP reagent to an acceptable level.

SUMMARY

This invention provides a system that satisfies the above needs. The system uses a liquid reagent comprising NAD (or NADP) coenzyme, wherein the reagent has an extended shelf life. The reagent is intended for the quantitative determination of lactate dehydrogenase or lactate in a LD-L assay. The reagent comprises the NAD (or NADP) coenzyme, and a sulfhydryl compound capable of counteracting the inhibitory effects of the degradation products of NAD (NADP) on LD-L activity. The reagent has a pH less than about 3½. The preferred pH range is from about 1½ to about 2.

The sulfhydryl compound is in a sufficient amount that when the reagent is stored in the substantial absence of oxygen at a temperature in the range of from about 2° to about 8° C., the reagent for a period of at least about 2 years maintains a LD-L activity of at least about 90% of that of the reagent when the NAD coenzyme was first put in solution in the reagent. Preferably the sulfhydryl compound is in a sufficient amount that when the reagent is stored in the substantial absence of oxygen at a temperature of no more than about 25° C., the reagent has a shelf life (90% LD-L activity) of at least about 2 months.

Preferably the coenzyme reagent comprises:

(a) NADP coenzyme, in an amount of from about 200 to about 400 mM;

(b) at least about 40% v/v of a non-reactive aqueous component;

(c) an aqueous miscible polyol organic solvent in an amount of from about 45% to about 60% v/v; and (d) a sulfhydryl compound capable of counteracting the inhibitory effects of the degradation products of NAD (or NADP) on LD-L activity.

Preferably the sulfhydryl compound is placed in solution in the reagent more than about 15 minutes before the reagent is used in a LD-L assay.

The coenzyme reagent of the present invention can be used in an analytical method for the quantative determination of lactate dehydrogenase or lactate in a LD-L assay, the method comprising the step of mixing:

(a) a first solution containing the enzyme lactate dehydrogenase.

(b) a second solution containing the substrate lactic acid or lactate; and (c) a third solution being the coenzyme reagent of the present invention; to form a combined assay LD-L mixture.

The coenzyme reagent of the present invention is preferably prepared by the steps of:

(a) selecting components comprising:
  (i) a non-reactive aqueous component;
  (ii) an aqueous miscible polyol organic solvent, the solvent being a liquid at least at room temperature when dissolved in the aqueous component;
  (iii) NAD (or NADP) conezyme; and
  (iv) a sulfhydryl compound capable of counteracting the inhibitory effects of the degradation products of NAD (or NADP) on LD-L activity;

(b) mixing the components to form the reagent, the components being in such proportions that the aqueous component is in an amount of at least about 40% v/v, the solvent is in an amount of from about 45% to about 60% v/v; and (c) maintaining the pH of the NAD (or NADP) reagent at less than about 3½; the sulfhydryl compound being in a sufficient amount such that, when the reagent is stored in the substantial absence of oxygen at a temperature in the range of from about 2° to about 8° C., the reagent for a period of at least about 2 years maintains a LD-L activity of at least about 90% of that of the reagent when the NAD (or NADP) coenzyme was first put into solution in the reagent.

Examples of suitable sulfhydryl compounds are given, and the preferred concentration ratios of NAD:-sulfhydryl compounds are given for three sulfhydryl compounds.

DRAWINGS

These and other features, aspects, and advantages of the present invention will become better understood with reference to the following description, appended claims, and accompanying drawings where:

FIGS. 1–4 are HPLC chromatographs of (1) a fresh NAD reagent; (2) a NAD reagent stored at 4° C. for about 1 year; (3) a fresh NAD reagent stressed at 41° C. for 11 days; and (4) the NAD reagent of sample (3), containing an additional 170 mM N-acetyl-cysteine, and stressed at 41° C. for 11 days; respectively.

FIGS. 5–8 show the decay of LD-L activity with time, for NAD reagent samples subjected to thermal stress at 25°, 32°, 37° and 41° C., respectively; some of the NAD reagent samples contain various sulfhydryl compound enhancers.

FIG. 9 is a plot showing the linearity of LD-L chemistry for NAD reagent samples containing various sulfhydryl compound enhancers.

FIG. 10 is an Arrhenius plot for NAD reagents to reach 90% LD-L activity.

DESCRIPTION

Figure 3:
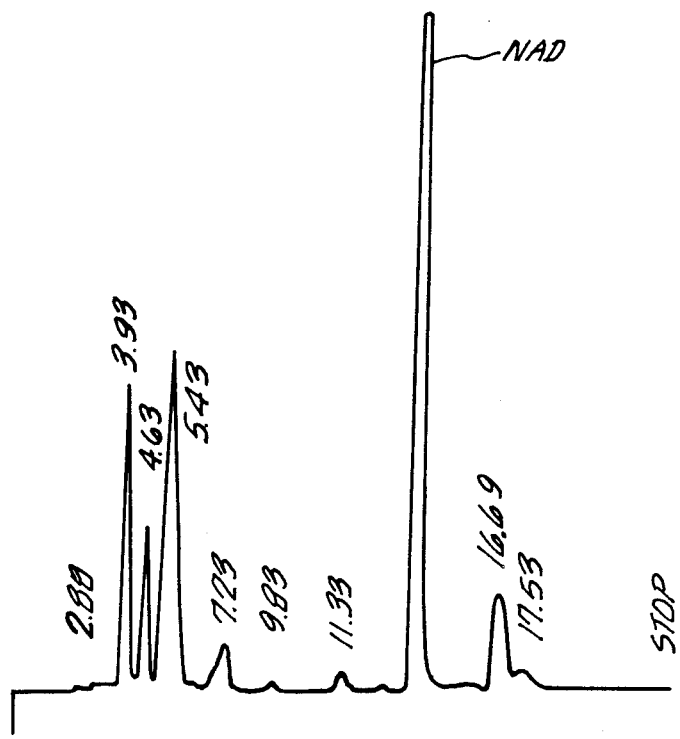
Figure 4:
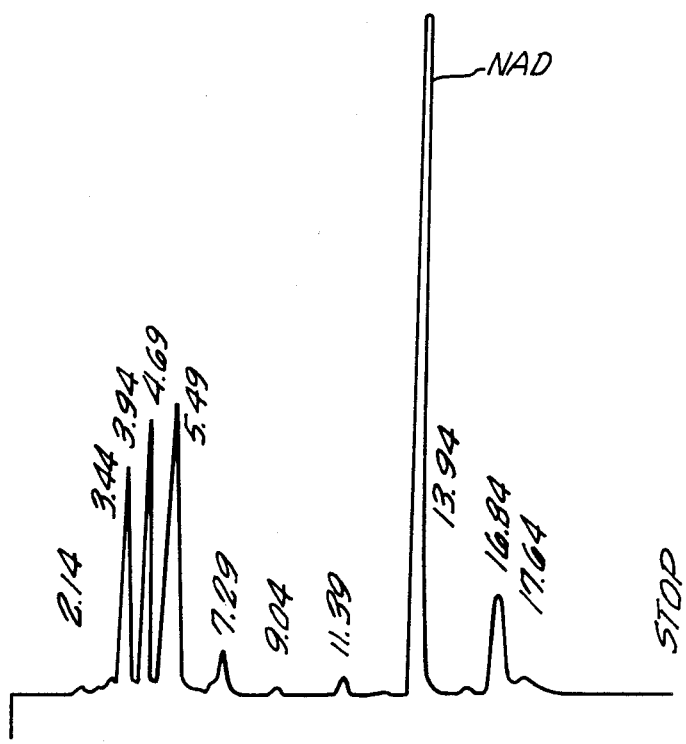
Figure 5:
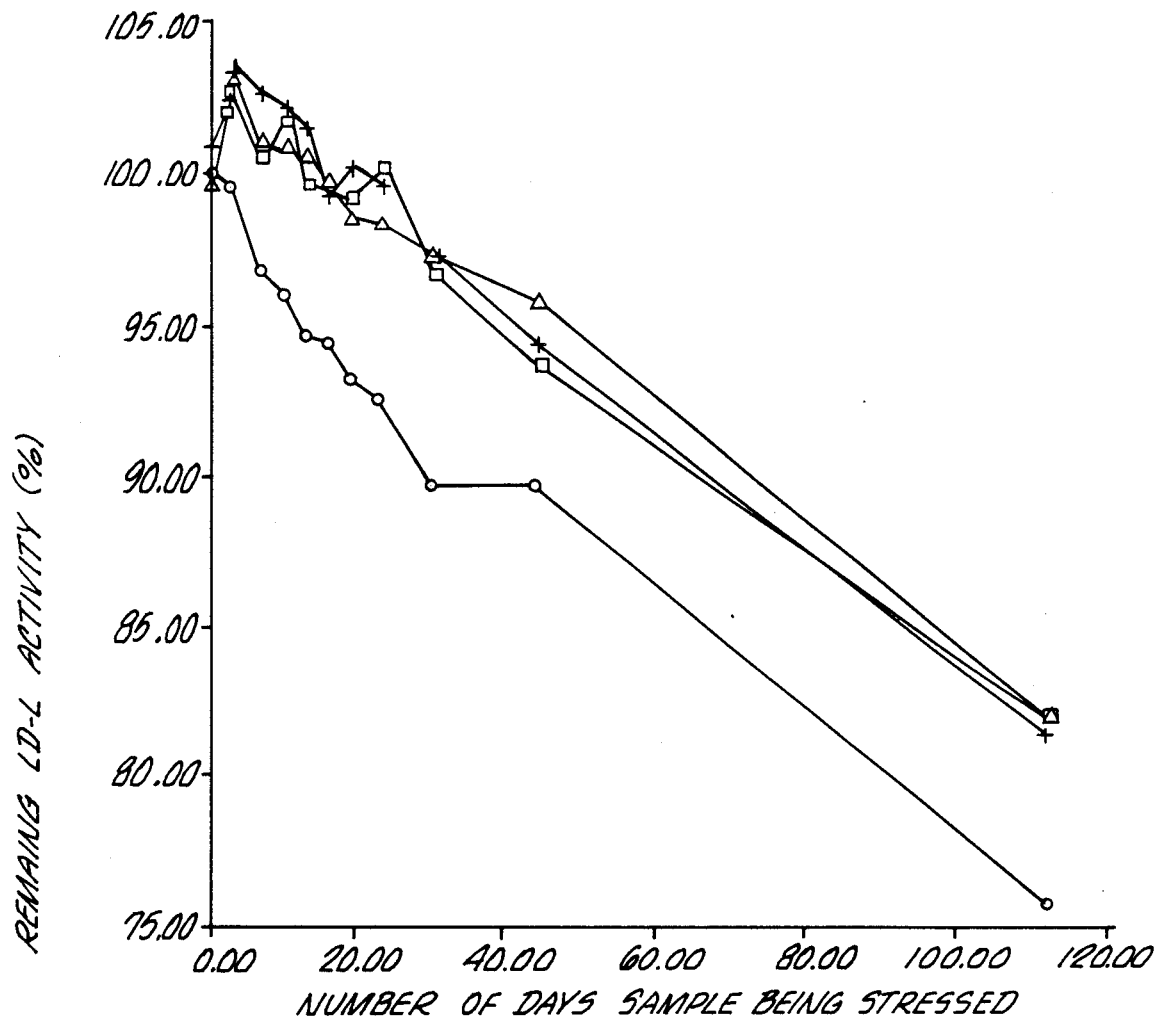
Figure 1:
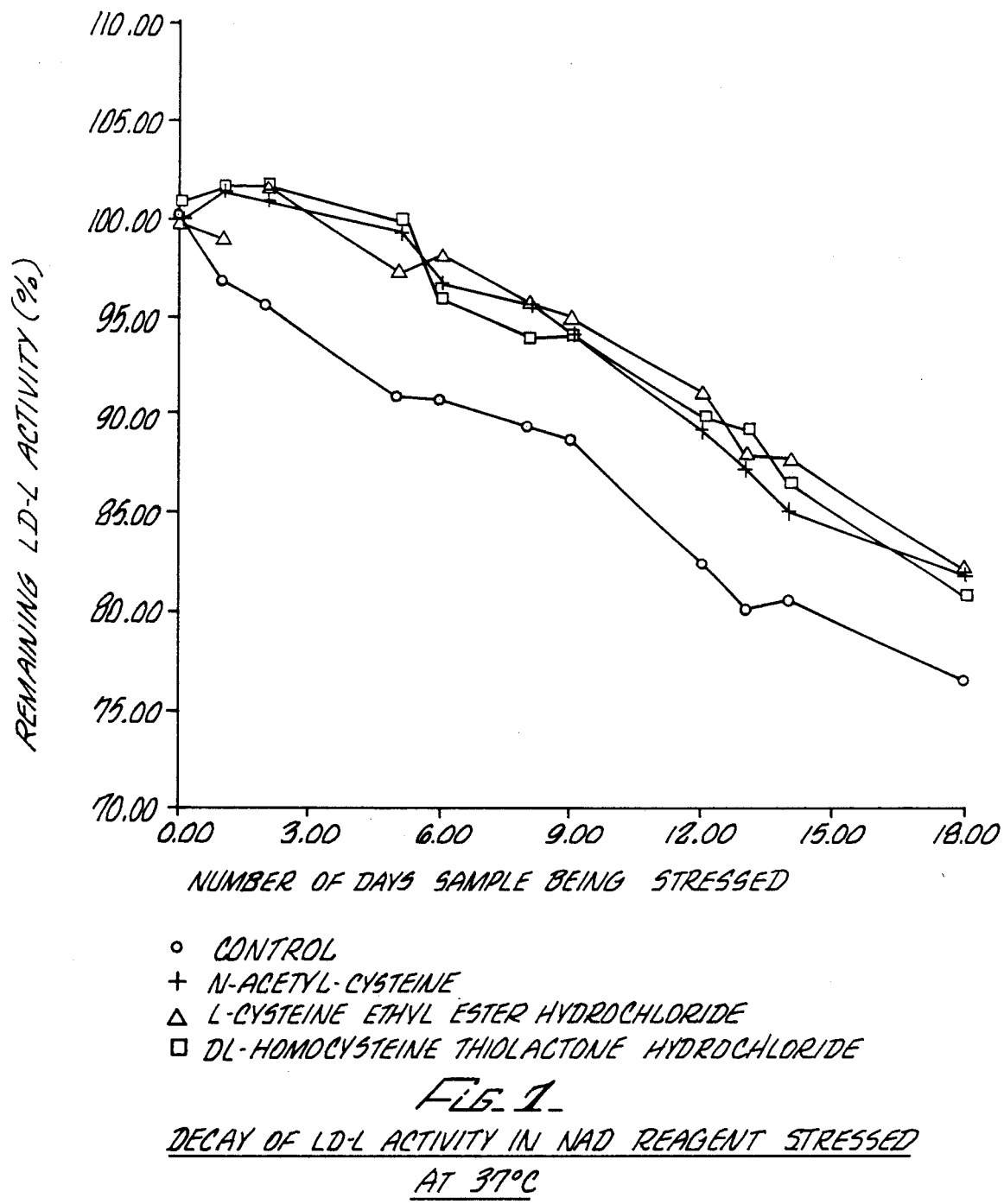
Figure 8:
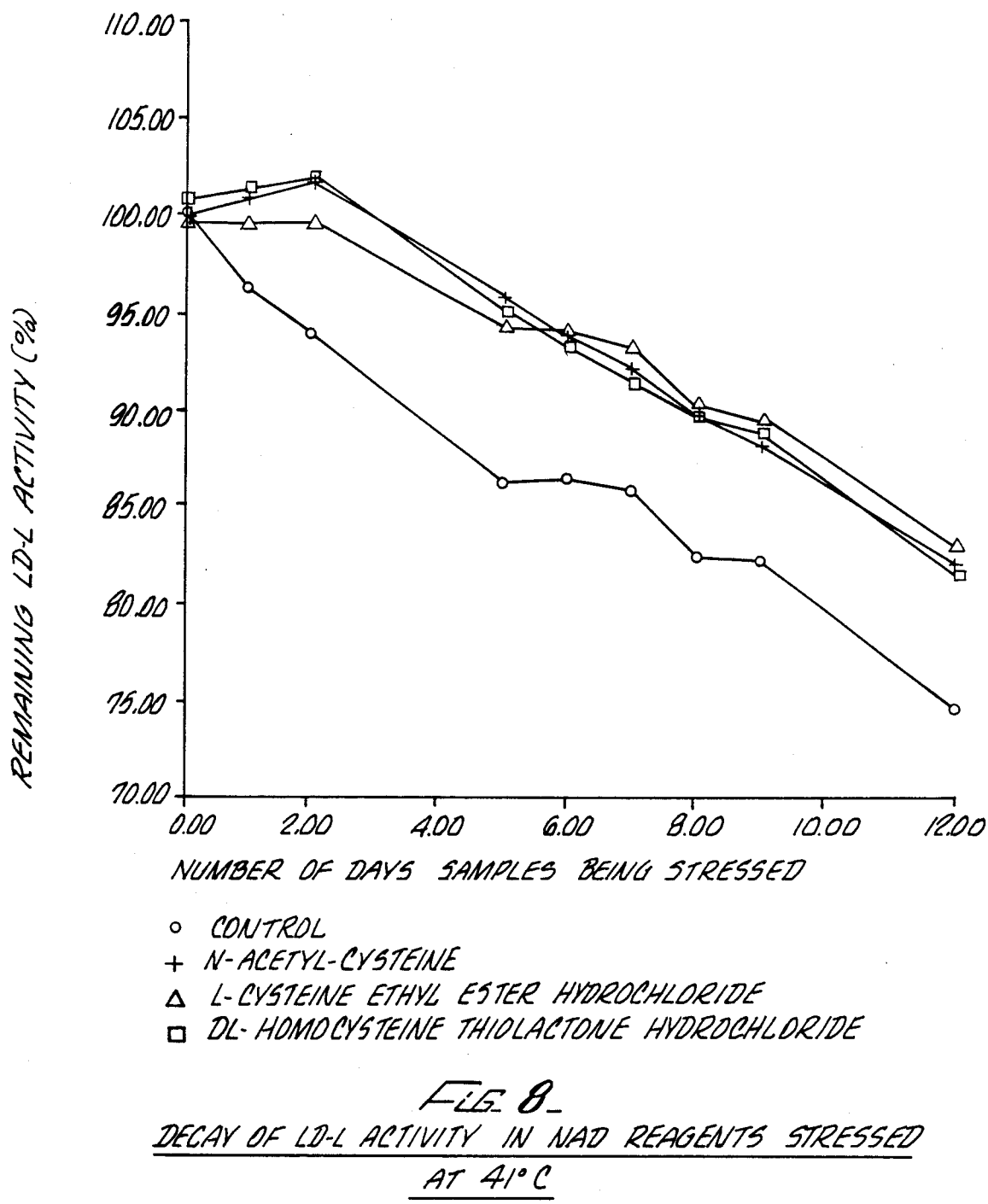

Sulfhydryl compounds are not known to substantially enhance LD-L activity. Therefore it is surprising to discover that a labile sulfhydryl compound, when added to a liquid NAD (or NADP) coenzyme reagent, with the pH of the coenzyme reagent maintained at no more than about 3½, greatly extends the shelf life of the reagent. The shelf life is defined as the period during which the coenzyme reagent maintains at least 90% of its LD-L activity, when compared to a freshly prepared reagent with the same coenzyme concentration to begin with (proper storage at 2°–8° C. is assumed).

Although the following discussion refer to the coenzyme NAD, they apply with equal force to the related coenzyme NADP.

Suitable sulfhydryl compounds are selected on the basis of their LD-L inhibitor suppression efficiency, cost, solubility, and lack odor. Suitable sulfhydryl compounds include:

1. L-cysteine ethyl ester hydrochloride (CEE)
2. N-acetyl-cysteine (NAC)
3. DL-homocysteine thiolactone hydrochloride (HCTL)
4. L-cysteine
5. Mercaptoethanol (ME)
6. Dithiothreitol (DTT)
7. Dithioerythritol (DTE)
8. Aminoethylisothiouronium bromide (AET)
9. Glutathione (GSH)
10. Thioglycolic acid (TGA)
11. N-Guanyl-L-cysteine
12. N-Guanyl-DL-isocyanate
13. N-Acetyl-S-guanyl-L-cysteine
14. N-Acetyl-S-benzyl-L-cysteine
15. N,S-Diguanyl-L-cysteine
16. S-Carbamoyl-L-cysteine
17. S-Carboxymethyl-L-cysteine
18. L-Thiazolidine-4-carboxylic acid
19. S-Guanyl-L-cysteinehydantoin
20. S-Acetylguanyl-DL-cysteineazlactone
21. 2-Imino-L-cysteinehydantoin
22. N-Acetyl-DL-homocysteinethiolactone
23. 1,3 Dimercapto-2-propanol
24. 2,3 Dimercapto-1-propanol
25. 1,2 Dimercapto-ethane
26. L-Cysteinemethyl ester
27. L-Cysteineethyl ester
28. N-Acetyl-DL-isocysteine
29. Polyethyleneglycol dimercaptoacetate
30. Thioglucose
31. Thioglycerol It was found that the sulfhydryl compounds take time to react with the breakdown products of NAD. Adding the sulfhydryl compound directly to the LD-L assay mixture has some beneficial effect. But the results are inferior to those achieved by adding the sulfhydryl compound to the NAD reagent as soon as possible. In a typical present day LD-L assay, the substrate reagent is mixed with the NAD reagent, and the mixture is preincubated for a short period of time (in the order of 3–5 minutes), then the solution containing the enzyme LD is added, and the measurement of the rate of change in the absorbance immediately begins. The short preincubation period is insufficient for the sulfhydryl compound to react thoroughly with the NAD degradation products. Therefore it is preferable that the sulfhydryl compound be added to the NAD reagent, and preferably as soon as possible.

The sulfhydryl compound is preferably placed in solution in the NAD reagent no more than about one week after, more preferably no more than about one day after, even more preferably no more than about one hour after, and most preferably at the same time when, or before, the NAD coenzyme is placed in solution in the reagent. That is, if the sulfhydryl compound is added to the coenzyme reagent during the manufacturing process, it is preferred that the sulfhydryl compound be put into solution contemporaneously as, or before, the NAD coenzyme is put in solution in the reagent.

Moreover, the sulfhydryl compound is preferably placed in solution in the NAD reagent at least about 15 minutes before, more preferably at least about one hour before, and most preferably at least about one day before, the NAD reagent is used in a LD-L assay. That is, if the sulfhydryl compound is added to an existing NAD enzyme reagent solution, e.g., so as to rejuvenate an aged conenzyme reagent, time should be allowed for the sulfhydryl compound to react sufficiently with the degradation products of the coenzyme.

The concentration of the sulfhydryl compound in the NAD reagent is also important. In general, the guideline is to use the smallest amount of the sulfhydryl compound that gives adequate LD-L inhibitor suppression. Adequate LD-L inhibitor suppression is also defined as maintaining the LD-L activity of the coenzyme reagent solution at 90% of that of the coenzyme reagent when fresh, for a period of at least 2 years, assuming proper storage at 2°-8° C. The sulfhydryl concentration should be kept at a minimum because the sulfhydryl compounds listed above are all quite reactive, especially at elevated temperatures. Mishaps during shipment or storage, in which the NAD reagent (with its sufhydryl component) is subject to elevated temperatures, may lead to unpleasant and predictable consequences. However, there should be a sufficient amount of the sulfhydryl compound to maintain the LD-L activity of the NAD reagent. Also, it was found that each sulfhydryl compound has its own optimal concentration range, depending on the coenzyme concentration in the reagent. The particular concentration can be determined experimentally, by well known methods.

For example, the following concentration ranges for three sulfhydryl compounds are based on a NAD reagent having the coenzyme dissolved in a 53% (v/v) glycerol in water solution. The amount of the coenzyme is from about 200 to about 400 mM. L-cysteine ethyl ester hydrochloride (CEE) has a preferred concentration ranging from about 60 to about 100 mM, most preferred about 80 mM. That is, the concentration ratio of NAD:CEE is preferably in the range of from about 2:1 to about 6½:1, with an optimal ratio of about 4:1. N-acetyl-cysteine (NAC) has a preferred concentration ranging from about 80 to about 260 mM, most preferred about 170 mM. That is, the concentration ratio of NAD:NAC is preferably in the range of from about ¾:1 to about 5:1, with an optimal ratio of about 2:1. DL-homocysteine thiolactone hydrochloride (HCTL) has a preferred concentration ranging from about 170 to about 500 mM, most preferred about 340 mM. That is, the concentration ratio of NAD:HCTL is preferably in the range of from about ½:1 to about 2½:1, with an optimal ratio of about 1:1.

The above preferred concentration ratios also apply to NADP conenzyme reagents.

The pH of the NAD reagent is also important. Accelerated degradation data showed that the NAD reagent is highly unstable at a pH above 5, especially at elevated temperatures. Moreover, the degradation products at pH above 5 may be quantitatively different than those formed at a pH of say, 3½ or lower. The degradation products formed in a NAD reagent stored at a pH of above 5 can, in addition to their LD-L inhibitory effects, interfere with photometric assay determinations. Accelerated thermolysis data at 41° C. showed that the degradation products possess an intense yellow or brown color in a NAD reagent having a pH of about 5.45. This coloration is not present in NAD reagents at pHs below 3½ and subject to the same thermal stress.

The preferred pH range for the NAD reagent of the subject invention, for the purpose of achieving long shelf life, is from about 1 to about 3½. The most preferred pH range is from about 1½ to about 2. The unadjusted pH of a NAD reagent, having about 330 mM of NAD in a solution of 53% (v/v) glycerol in water, and containing any of the three most preferred sulfhydryl compounds in an amount within the ranges described above, is within the pH range of 1½ to about 2.

It is known that the sulfhydryl compounds are easily oxidized in air. The oxidized sulfhydryl compounds do not suppress the inhibitory effect of NAD degradation products on LD-L activity. Therefore the current practice of storing the NAD reagent in the absence of oxygen, e.g. by packaging and sealing the reagent in a nitrogen blanket, should be continued. The current practice of storing the NAD reagent in a temperature range of from about 2° to 8° C. should also be continued.

Although the examples given herein are related to UV methodologies, the sulfhydryl compound enhanced NAD (or NADP) coenzyme reagents can also be used in colorimetric determinations involving the LD-L system.

It is predicted that a liquid NAD or NADP reagent according to the present invention can have a shelf life (at least 90% LD-L activity) of at least about 2 years, and possibly up to 4 years, when properly stored at 2°-8° C. The advantages of having a liquid NAD or NADP reagent having a long shelf life are many. In health care applications, e.g., in the hospital laboratory, many assays are required on a STAT basis, i.e., the test has to be done right away. Therefore, the assay reagents must be ready for use all the time. It is not practical to prepare fresh batches of coenzyme reagents for each test to assure assay reliability. Also, less stringent quality control parameters (e.g., temperature control), during both manufacturing and shipping, are required for the liquid coenzyme reagents of the present invention, in comparison to prior liquid NAD (or NADP) coenzyme reagents. This leads to lower cost for the products. The user can be assured that the convenient, ready to use liquid coenzyme reagent of the present invention can be used to give reliable results.

EXAMPLES

A. Reagents

In the following examples, unless otherwise indicated, the following reagent formulations were used:

1. Formulations
   a. Substrate-Buffer Reagent- aqueous solution of: sodium lactate, 52 mM; TAPS buffer (tris-(hydroxymethyl) methylamine propane sulfonic acid), 100 mM; sodium azide as preservative, 2 gm/l; with a pH of about 8.9, adjusted by adding NaOH and/or acetic acid as necessary.
   b. NAD Reagent- nicotinamide adenine dinucleotide, lyophilized, dissolved in 53% (v/v) glycerol in water, with a NAD concentration of 327 mM, pH was unadjusted (about 1.7 to 2.0).
   c. LD Enzyme Reagent- a serum based standard reagent marketed under the trademark Decision 3, containing 320–450 IU/l of the enzyme LD, supplied by Beckman Instruments of Fullerton, Calif.
2. Suppliers Lyophilized NAD is available from two sources, namely Boehringer Mannheim of Indianapolis, Ind. and Kyowa Hakko Kogyo Co., Ltd. of Tokyo, Japan. The ADH assay reagent kit (ethyl alcohol stat pack), and the TAPS buffer are available from Calbiochem Behring of La Jolla, Calif. The sulfhydryl compounds, namely L-cysteine, N-acetyl-cysteine, L-cysteine ethyl ester hydrochloride, and DL-homocysteine thiolactone hydrochloride, and the lactic acid for forming the substrate/buffer reagent, are available from Sigma of St. Louis, Mo. Glycerol is available from Fisher Scientific of Pittsburgh, Pa.

B. Methodologies

1. HPLC Studies of NAD reagent

HPLC (High Performance Liquid Chromatography) studies were performed on a Beckman HPLC system equipped with two Model 100A pumps, a Model 421 controller, a model 165 detector, and an Altec data integrator (from Altec Beckman of Berkeley, Calif.).

The sample analyzed was diluted with deionized water to a concentration of approximately 1 to 2.5 mg/ml. The sample dilution was performed exactly 2 minutes prior to injection. In each run, about 20 μl of the diluted sample were injected into a octododecyl silica column (Altec 5 micron Ultrasphere, 4.6 mm×25 cm), and were eluted at a flow rate of about 1 ml/min. in a reverse mode. The analytes were eluted with a two buffer system gradient consisting of Buffer A (10 mM sodium phosphate, pH 7.0) and Buffer B (10 mM sodium phosphte, pH 7.0, with 20% v/v methanol). The gradient system was programmed as follows: 2 min. of 100% Buffer A, 15 min. of 50% Buffer B (gradient), 2 min of 100% Buffer B, and 5 min. of 100% Buffer A.

Nucleotide peaks were detected by absorbance at 260 mm (both nicotinamide and adenosine absorb strongly at this wavelength). Quantitation of various peak elutes was computed by integration of the area under the peaks.

2. Thermolysis of NAD Reagent

Samples of NAD reagents were subjected to thermal stress in order to collect accelerated degradation data. In each run, 2 ml of the reagent solution of the coenzyme was stored in a 5 ml capacity polyethylene vial with a screw type seal-tight cap, and the vial was sealed under nitrogen. The sample was then incubated at a preselected temperature for the requisite period of time.

3. LD-L Activity Assays

All of the LD-L activity assays were run on a COBAS-BIO centrifugal analyser, supplied by Roche Diagnostic Systems of Nutley, N.J. This is an automatic analyzer which performs the necessary volume measurements and mixing, preincubation, and rate measurements automatically. The NAD reagent, substrate-buffer, and LD enzyme were placed respectively as sample, reagent, and start reagent in the COBAS machine. The main instrument parameter settings on COBAS were as follows: 7 μl sample, 195 μl reagent, 10 μl start reagent, 235 μl final volume, preincubation temperature at 37° C., and absorbance monitored at 340 nm. The NAD sample and substrate buffer were mixed and incubated at 37° C. for 3 minutes, and the LD enzyme was added. The first absorbance reading was taken at 60 seconds and continued for every 10 seconds for a total of 16 absorbance readings. All samples were run in triplicates, and the result reported is the average of the three.

The above volume ratio of substrate-buffer: NAD was 27.9:1. The acceptable range is about 26 to about 31:1. The volume ratio of combined reagent: LD enzyme was 20.7:1. The final concentrations in the assay mixture were approximately: 43 mM lactic acid; TAP buffer 80 mM; NAD 11 mM; pH 8.5±0.2.

4. ADH quantitation of NAD

Alcohol dehydrogenase (ADH) activity assay was used to determine the NAD concentration in NAD coenzyme reagent samples. In this assay, in the presence of ADH and excess alcohol substrate, the conversion of a limited amount of dilute NAD sample to NADH was left to completion. At the endpoint, the NADH formed which was equal to the initial concentration of NAD was calculated using the known molar extinction coefficient of $6.22 \times 10^3$ cm$^{-1}$. The NAD concentration was read off the standard curve for absorbance. ADH assays were run on the previously described COBAS analyzer with the major instrument parameters set as follows: incubation temperature at 30° C., type of analysis 3, wavelength 340 nm, 3 μl of 1:100 diluted NAD as sample, 320 μl of ADH as reagent, 15 μl of ethyl alcohol as start reagent. Sample and reagent were mixed and incubated for 60 seconds. The absorbance reading was taken 1 second after the addition of start reagent and monitored every 40 seconds for a total of 800 sec. By then the reaction showed completion. All samples were run in triplicates, and the result reported is the average of the three.

EXAMPLE 1

HPLC Study of NAD Degradation

Four NAD samples were studied using the HPLC procedure described above. They were (1) freshly prepared NAD reagent; (2) NAD reagent stored at 4° C. for about 1 year; (3) freshly prepared NAD reagent stressed at 41° C. for 11 days; (4) the NAD reagent in sample (3), containing an additional 170 mM of N-acetyl cysteine, and stressed at 41° C. for 11 days. The results are presented in FIGS. 1–4, which correspond to the four samples above.

Fresh NAD is characterized by the predominate peak (95%) with approximately 13.8±0.1 minute retention time.

The NAD sample stored at 4° C. over a year shows at least 6 major degradation products, characterized by the 4.0 min (4%), 4.6 min (2.2%), 5.7 min (11.9%), 7.6 min (3.2%), and 11.4 min (2.2%) peaks preceeding the NAD peak at 13.8 min (72.5%), and another degradation product peak at 16.8 min. (3.5%). Note that the percentage inside the parenthesis represents a relative concentration unit and not a true percentage of the quantity present in the sample.

The NAD sample stressed at 41° C. for 11 days (accelerated thermolysis) showed twice the amount of breakdown products with concomitant decrease of NAD as compared to the one year sample. The amount of the breakdown product relative to each other remained approximately the same.

The above sample in the presence of N-acetyl-cysteine under the same thermal stress conditions showed a similar extent of NAD degradation (43.5±0.5%) as shown in FIG. 3. But there were significant quantitative differences in the chromatographs in FIGS. 3 and 4. Peak 2 increased from 6.2 percent to 10.2 percent (64.5% increase) when the sulfhydryl compound was present. There were also small changes in the quantity of peak 1 and peak 3. A new small peak at 3.44 min (FIG. 4) also appeared when the sulfhydryl compound is present. The peak was small but the result was consistently reproducible in every sample where N-Acetylcysteine was present. The increase of peak 2 may be attributed to the reaction of N-acetyl cysteine with one of the degraded NAD products which result in a new derivatized product having a higher absorption coefficient.

The results demonstrate that a sulfhydryl compound such as N-acetyl cysteine does not prevent or stabilize the degradation of NAD. The results also show that the sulfhydryl compound alters the products of degradation of NAD.

EXAMPLE 2

ADH quantitation of NAD samples

The following samples were assayed:
(1) fresh NAD reagent (100%);
(2) fresh NAD reagent, but with only 80% of the NAD concentration in sample 1;
(3) fresh NAD reagent, but with only 54% of the NAD concentration in sample 1. (samples 1–3 were prepared from Boeringer Mamiheim lyophilized NAD.)
(4) aged NAD reagent, stored at 5° C. for 9 months.
(5) sample 4, stressed at 41° C. for 6 days.
(6) aged NAD reagent, stored at about 4° C. for over one year. (samples 4–6 were prepared from lyophilized NAD supplied by Kyowa Hakko Co., Ltd.)

The NAD concentration was measured, using the ADH assay procedure described above. The results are summarized in Table 1. The results show that NAD reagents degrade over time. NAD reagents stored at about 4° C. for 9 months to 1 year have only 75–80% NAD remaining. NAD reagent stressed at 41° C. for 6 days has less than half of its original NAD.

TABLE 1

Quantitation of NAD samples by ADH Assay

| Sample No. | Sample | Theoretical Value (mM) | Experimentally determined Value (mM) | NAD remaining (% of theoretical) |
|---|---|---|---|---|
| 1 | fresh, 100% | 327 | 323 | 98.8 |
| 2 | fresh, 80% | 262 | 260 | 99.2 |
| 3 | fresh, 54% | 177 | 174 | 98.4 |
| 4 | 5° C., 9 months | 327 | 245 | 75.0 |
| 5 | sample 4, 41° C., 6 days | 327 | 159 | 48.7 |
| 6 | 4° C., 1 year | 327 | 262 | 80.0 |

EXAMPLE 3

LOSS of LD-L Activity in Aged NAD Reagent

The LD-L activity of the six samples in Example 2 above were assayed, using the procedure described above. The results are shown in Table 2. The activity of sample 1 (fresh NAD 100%) was used as the reference and the activity of the other samples were compared against it. The NAD concentrations determined in Example 2 above are also listed in Table 2, as a percentage of the theoretical amount of NAD in the fresh, 100% solution.

The results demonstrate that there is a loss in LD-L activity in aged, or thermally stressed NAD reagents. Further, such loss in activity is not due to the loss of NAD alone. Fresh NAD reagents with only 53 and 79% of NAD still gave almost 100% LD-L activity. In contrast, aged and stressed samples which have 49 to 80% NAD only give 81 to 90% LD-L activity. Moreover, the NAD is still in large excess in all of the assay samples. Therefore, the loss of NAD in the samples was not responsible for the loss of LD-L activity.

TABLE 2

LD-L Activities of NAD samples

| Sample No. | Sample | % NAD Concentration | LD-L Activity % |
|---|---|---|---|
| 1 | fresh, 100% | 98.8 | 100.0 |
| 2 | fresh, 80% | 79.4 | 99.6 |
| 3 | fresh, 54% | 53.1 | 99.0 |
| 4 | 5° C., 9 months | 75.0 | 90.4 |
| 5 | sample 4, 41° C., 6 days | 48.7 | 80.8 |
| 6 | 4° C., 1 year | 80.0 | 89.9 |

Note: % NAD Concentration, 100% = 327 mM NAD

The above results strongly suggest that the degradation products in the aged NAD samples are inhibitory to the LD-L activity.

EXAMPLE 4

Inhibitory Effect of NAD Degradation Products on LD-L Activity

To confirm the finding that the degradation products in the aged NAD samples were inhibitory to LD-L activity, the experiment in Example 3 was repeated, except with the volumes of NAD reagents used being increased to 3 times that used in Example 3. The results were compared to those using one colume of NAD in Table 3. Again the LD-L activity of freshly prepared NAD (100%) reagent was used as the reference.

The results show that increasing the amounts of aged NAD in the assay further decreases the LD-L activity.

TABLE 3

LD-L Activity Inhibition by Increase NAD Dosage

| Sample No. | Sample | LD-L Activity, % 3 vol. NAD | LD-L Activity, % 1 vol. NAD |
|---|---|---|---|
| 1 | fresh, 100% | 95.7 | 100% |
| 2 | fresh, 80% | 99.0 | 99.6 |
| 3 | fresh, 54% | 100.0 | 99.0 |
| 4 | 5° C., 9 months | 85.0 | 90.4 |
| 5 | sample 4, 41° C., 6 days | 74.0 | 80.8 |
| 6 | 4° C., 1 year | 85.0 | 89.9 |

The above results confirm the finding that the breakdown products in aged or thermally stressed NAD samples are inhibitory to the LD-L activity.

EXAMPLE 5

Effect of L-Cysteine on LD-L Activity of Aged NAD Reagents

L-cysteine was added in different concentrations to the substrate/buffer solutions in Example 3 above, immediately before the assay. The L-cysteine concentrations shown in Table 4 are with reference to the substrate/buffer solution. An extra sample (no. 7) was also assayed, being sample 4 stressed at 41° C. for 12 days. The LD-L activity was then measured as described above. It was found that when 120 mM of L-cysteine was added, it was necessary to adjust the pH of the assay composition to come within 8.5±0.2. Again the activity of fresh, 100% NAD was used as the reference for comparing the results of the assays.

The results, shown in Table 4, show that 120 mM L-cysteine added to the substrate/buffer solution does have some effect, in improving the LD-L activity by 3-5%. But this increase in activity is insufficient to bring the activity of seriously degraded NAD reagents (e.g. samples 5 and 7) to within an acceptable range (at least 90% LD-L activity).

TABLE 4

Effect of L-Cysteine on LD-L Activity of Aged NAD Reagents

| Sample No. | Sample | L-Cysteine Concentration in Substrate/Buffer Reagent | | | |
|---|---|---|---|---|---|
| | | 0 mM | 60 mM | 120 mM (no pH adjustment) | 120 mM pH adjusted to 8.5 ± 0.2 |
| | | LD-L Activity (%) | | | |
| 1 | fresh, 100% | 100.0 | 100.0 | 100.0 | 100.0 |
| 2 | fresh, 80% | 99.5 | 99.3 | 99.4 | 99.4 |
| 3 | fresh, 54% | 97.6 | 97.1 | 100.5 | 99.6 |
| 4 | 5° C., 9 months | 92.8 | 95.3 | 99.4 | 94.7 |
| 5 | sample 4, 41° C., 6 days | 82.1 | 85.2 | 87.4 | 85.0 |
| 6 | 5° C., 1 year | 92.0 | 95.2 | 97.8 | 94.1 |
| 7 | sample 4, 41° C., 12 days | 71.6 | 73.2 | 76.6 | 77.0 |

EXAMPLE 6

DECAY OF LD-L ACTIVITY over time

The change in LD-L activity over time, in samples of NAD reagents containing three sulfhydryl compounds were compared against that in a fresh NAD reagent sample (control) The following sulfhydryl compounds were added to separate NAD reagent samples to give a final concentration of 170 mM: (1) N-acetyl cysteine, (2) L-cysteine ethyl ester hydrochloride, (3) DL-homocysteine thiolactone hydrochloride. The pH of the NAD reagents were not adjusted after the addition of the sulfhydryl compounds. The pH for the samples above were 1.81, 1.92, and 1.72 respectively. The 170 mM concentration corresponds to about 5 mM of the sulfhydryl compound in the LD-L assay composition.

Each of the samples was stored in a screw-top plastic vial as described above and incubated at 41° C., 37° C., 32° C. and 25° C., respectively, for collecting accelerated degradation data as previously described. The LD-L activity of each sample was studied over a period of days, using the procedure previously described. The LD-L activity of freshly prepared NAD stored at about 4° C. was used as reference (100%), so as to minimize day-to-day instrument variations.

The amount of NAD degradation in the samples was also monitored using the ADH assay described previously. The results are listed in Table 5.

FIGS. 5-8 show the LD-L activity of the NAD formulations as a function of time at 4 stressed temperatures, at 25°, 32°, 37° and 41° C. respectively. It is interesting to note that the test formulations (with the sulfhydryl compound enhancers) show no loss in LD-L activity initially, for a period of a few days to two weeks depending on the stressed temperature (faster deterioration at higher temperatures). After the lag period the decay in LD-L activity of the test formulations run almost in parallel to that of the control (without sulfhydryl compound). All three test formulations performed similarly within experimental error at all four stressed temperatures.

It is well known that sulfhydryl reagents can readily be oxidized by air, particularly at elevated temperatures. It appears that while sulfhydryl compounds are still unoxidized in the early stage of storage, they are active and counteract the effects of the inhibitors formed fromm NAD degradation. After a period of storage at elevated temperature, all the sulfhydryl compounds eventually have been either oxidized or degraded, and the decay of LD-L activity follows the course parallel to that of the control.

TABLE 5

NAD Degradation Under Stressed Conditions

| | Sample | Days | NAD remaining | LD-L Activity |
|---|---|---|---|---|
| A. | 41° C. | | | |
| 1. | Control | 2 | 72 | 94 |
| 2. | Control | 5 | 54 | 86 |
| 3. | Control | 7 | 51 | 86 |
| 4. | w/CEE | 7 | 55 | 93 |
| 5. | w/NAC | 7 | 62 | 92 |
| 6. | w/HCTL | 7 | 56 | 91 |
| B. | 37° C. | | | |
| 1. | Control | 5 | 63 | 91 |
| 2. | w/CEE | 12 | 54 | 91 |
| 3. | w/NAC | 12 | 56 | 89 |
| 4. | w/HCTL | 12 | 49 | 80 |
| C. | 32° C. | | | |
| 1. | Control | 12 | 64 | 91 |
| 2. | Control | 19 | 53 | 87 |
| 3. | w/CEE | 19 | 57 | 94 |
| 4. | w/NAC | 19 | 63 | 93 |
| 5. | w/HCTL | 19 | 62 | 92 |
| 6. | w/CEE | 21 | 55 | 93 |
| 7. | w/NAC | 21 | 58 | 92 |
| 8. | w/HCTL | 21 | 53 | 91 |

Note: The NAD remaining was based on the ADH assay using the activity of the control at 4° C. as a reference, the quantities shown do not take into account the possible postive bias of chromogenic derivatives having absorbance at 340 nM which may be formed from the reaction of the sulfhydryl compound with NAD degradation products. Therefore the NAD remaining listed above for sulfhydryl-compound-added NAD reagent formulations may be about 4-10% higher than the actual value.

EXAMPLE 7

Linearity of LD-L Chemistry

Six LD enzyme standards, having concentrations of 39, 99, 272, 435, 603, and 1206 IU/l of the enzyme lactate dehydrogenase, respectively, were assayed using 5 difference NAD reagent samples:

(1) Control, freshly prepared NAD reagent
(2) sample 1, stressed at 37° C. for 8 days
(3) sample 1+CEE, stressed at 41° C. for 8 days
(4) sample 1+NAC, stressed at 41° C. for 8 days
(5) sample 1+HCTL, stressed at 41° C. for 8 days The results were plotted in FIG. 9, as Absorbance Change vs. Enzyme Concentration. Plots for all samples showed excellent linearity up to 603 IU/l. The calibration line curved down slightly at the higher calibration point. The slopes of the samples having sulfhydryl compound enhancers differ only slightly from, and the intercepts differ only less than 2 IU/l from, the control. Therefore unknown determinations based on the test formulations (with sulfhydryl compound enhancer) should be reliable.

EXAMPLE 8

Predicted Shelf life of Test Formulations Based on Arrhenius Plot

The rate constant of LD-L activity decay for various samples under different temperature conditions were calculated by least-square unweighted linear regression method. Both zero and first order decay models were tried. The latter model seemed to give a slightly better fit to the data. For the test formulations, since there was an initial lag phase in the decay curve, rate constant calculations were carried out using only those data points where decay becomes apparent. Thus, data points from Day 5 to 12, Day 5 to 18, and Day 7 to 21, and Day 15 to 111 are used for the test formulations at four stressed temperatures, 41° C., 37° C., 32° C., and 25° C. respectively. The rate constants calculated are listed in Table 6.

TABLE 6

NAD Degradation Rate Constants for NAD Reagents to Reach 90% LD-L Recovery

| Sample | Rate Constant (days) | | | |
|---|---|---|---|---|
| | 41° C. | 37° C. | 32° C. | 25° C. |
| 1. Control | 3.5 | 6.4 | 12.9 | 36.5 |
| 2. + CEE | 8.1 | 12.0 | 23.1 | 66.0 |
| 3. + NAC | 7.9 | 11.2 | 23.3 | 64.6 |
| 4. + HCTL | 7.0 | 11.3 | 22.6 | 64.3 |

The logarithm of rate constant verus reciprocal of temperature in degree Kelvin was plotted in FIG. 10. Only the NAC-added test formulation is shown on the plot because all three sulfhydryl compound added formulations have about the same decay rate constant. The data fit well with straight lines. Therefore it can be justified to use the Arrhenius equation to predict shelf life at other given temperatures by using the following equation:

$$\text{Log } R = \Delta H/kT + A$$

where R is the rate constant, $\Delta H$ the heat of activation, k the gas constant (1.987 cal°K.), T the temperature in degree Kelvin, and A a constant related to the entropy of degradation reaction.

From the slope, the heat of activation was calculated to be 27.1 and 24.7 Kcal/°K. for the control and the test formulation, respectively. Under the usual storing condition at 4° C. refrigeration, a NAD reagent (in 53% v/v glycerol in water) without sulfhydryl compound should have a 3 year shelf life. The modified formulation (with sulfhydryl compound) could further extend the shelf life for another year. Because of the high heat of activation energy, the stability of NAD reagent is extremely sensitive to temperature. Therefore, taking temperature variations into consideration, which one must encounter during production and shipping, the present precaution for claiming only a one-year LD-L reagent shelf life, although being conservative, may well be justified. Therefore a NAD reagent having a sulfhydryl compound enhancer (170 mM) should have a shelf life of at least two years. Table 7 lists the estimated shelf life (90% LD-L activity recovery) of the various formulations at different temperatures.

TABLE 7

Predicted Shelflife at Various Temperatures (to retain 90% LD-L activity)

| Storage Temp. (°C.) | Control | With CEE | With NAC | With HCTl |
|---|---|---|---|---|
| 4 | 1184 | 1512 | 1562 | 1555 |
| 5 | 992 | 1286 | 1327 | 1320 |
| 10 | 417 | 583 | 595 | 591 |
| 20 | 80 | 130 | 130 | 129 |
| 25 | 37 | 64 | 63 | 62 |
| 30 | 17 | 32 | 31 | 31 |
| 37 | 6.2 | 13 | 12 | 12 |

EXAMPLE 9

Effect of pH on LD-L activity of NAD reagents with Sulfhydryl Compound Enhancer

Another series of experiments were performed, using a NAD reagent formulation having 170 mM of N-acetyl cysteine. The unadjusted pH of the sample was about 1.85. The pH of five samples were adjusted, using hydrochloric acid or sodium hydroxide, as necessary, to 1.0, 1.85, 2.45, 3.47, and 5.44 respectively. The samples were thermally stressed at 41° C. The LD-L activity and NAD concentration of each sample were monitored over a period of time using the LD-L assay and ADH assay procedures described above. Five additional samples without the sulfhydryl compound were similarly monitored. The results were shown in Table 8. The LD-L activity and NAD concentration of the fresh NAD reagent without pH adjustment were used as reference for comparison purposes.

TABLE 8

Effect of pH on LD-L Activity of NAD reagents with sulfhydryl compound Enhancer

| | | Without N-acetyl cysteine | | With N-acetyl cysteine | |
|---|---|---|---|---|---|
| | pH of reagent | LD-L Activity % | NAD Remaining % | LD-L Activity % | NAD remaining |
| A. | Fresh NAD Reagent | | | | |
| | 1.00 | 98 | 82 | 99 | 97 |
| | 1.85 | 100 | 100 | 99 | 100 |
| | 2.45 | 100 | 100 | 99 | 96 |
| | 3.47 | 100 | 95 | 93 | 95 |
| | 5.44 | 96 | 86 | 62 | 84 |
| B. | 41° C., 2 days | | | | |
| | 1.00 | 88 | 80 | 96 | 83 |
| | 1.85 | 87 | 86 | 96 | 84 |
| | 2.45 | 85 | 86 | 97 | 85 |
| | 3.47 | 85 | 83 | 96 | 89 |
| | 5.44* (See note below) | 91 | 83 | 90 | 76 |
| C. | 41° C., 5 days | | | | |
| | 1.00 | 84 | 59 | 93 | 63 |
| | 1.85 | 82 | 69 | 93 | 67 |
| | 2.45 | 80 | 71 | 94 | 67 |
| | 3.43 | 78 | 71 | 94 | 67 |
| | 5.44* (See note below) | — | — | — | — |

Note: Color of NAD degradation products too intense for meaningful assay

The results demonstrate that pH is an important factor when a sulfhydryl compound is used to counteract the effects of the LD-L inhibitors formed from the degradation of NAD. The enhancer works well at pHs up to about 3½ but its performance is substantially worse at a pH of 5½. The preferable pH range is about 1 to about 3½. The unadjusted pH, of all of the NAD reagent formulations described above, containing any of the three most preferred sulfhydryl compounds, fall within this range.

Again it is noted that the sulfhydryl compounds tested did not prevent the breakdown of NAD (which is hydroxyl ion catalyzed). The data in Table 8 show that the amount of NAD degradation is comparable with or without the sulfhydryl compound.

It was noted that at pH 5.44, with or without the sulfhydryl compound, under thermal stress conditions, the NAD reagent samples were very unstable, and developed an intense yellow to brownish color, which intensity increased with time. Therefore the assay results shown for the samples at pH 5.44 may not be meaningful. Also it was noted that the yellow color was absent in the other NAD reagent samples which had lower pHs.

Although the present invention has been described in considerable detail with reference to certain versions thereof, other version are possible. Therefore, the spirit and scope of the appended claims should not be limited to the description of the preferred versions contained herein.

What is claimed is:

1. A liquid NAD coenzyme reagent with an extended shelf life, the reagent for use for the quantitative determination of lactate dehydrogenase or lactate in a LP-L assay, the reagent comprising NAD coenzyme, and a sulfhydryl compound capable of counteracting the inhibitory effects of the degradation products of NAP coenzyme on LP-L activity, the reagent having a pH of less than about 3½, and the sulfhydryl compound being in a sufficient amount that when the reagent is stored in the substantial absence of oxygen at a temperature in the range of from about 2° to about 8° C., the reagent for a period of at least about 2 years maintains a LD-L activity of at least about 90% of that of the reagent when the NAD coenzyme was first put in solution in the reagent.

2. A liquid NADP coenzyme reagent with an extended shelf life, the reagent for use for the quantitative determination of lactate dehydrogenase or lactate in a LD-L assay, the reagent comprising NADP coenzyme, and a sulfhydryl comound capable of counteracting the inhibitory effects of the degradation products of NADP coenzyme on LD-L activity, the reagent having a pH of less than about 3½, and the sulfhydryl compound being in a sufficient amount that when the reagent is stored in the substantial absence of oxygen at a temperature in the range of from about 2° to about 8° C., the reagent for a period of at least about 2 years maintains a LD-L activity of at least about 90% of that of the reagent when the NADP coenzyme was first put in solution in the reagent.

3. The NAD reagent of claim 1, wherein the sulfhydryl compound is selected from the group consisting of L-cysteine, Mercaptoethanol, Dithiothereitol, Dithioerythritol, Aminoethylisothiouronium bromide, Glutathione, Thioglycolic acid, N-Guanyl-L-cysteine, N-Guanyl-DL-isocyanate, N-Acetyl-S-guanyl-L-cysteine, N-Acetyl-S-benzyl-L-cysteine, N,S-Diguanyl-L-cysteine, S-Carbamoyl-L-cysteine, S-Carboxymethyl-L-cysteine, L-Thiazolidine-4-carboxylic acid, S-Guanyl-L-cysteinehydantoin, S-Acetylguanyl-DL-cysteineazlactone, 2-Imino-L-cysteinehydantoin, N-Acetyl-DL homocysteinethiolactone, 1,3 Dimercapto-2-propanol, 2,3 Dimercapto-1-propanol, 1,2 Dimercapto-ethane, L-Cysteinemethyl ester, L-Cysteineethyl ester, N-Acetyl-D-Lisocysteine, Polyethyleneglycol dimercaptoacetate, Thioglucose, and Thioglycerol.

4. The reagent of claim 1, or 2, wherein the sulfhydryl compound is L-cysteine ethyl ester hydrochloride.

5. The reagent of claim 1, or 2, wherein the sulfhydryl compound is N-acetyl-cysteine.

6. The reagent of claim 1, or 2, wherein the sulfhydryl compound is DL-homocy-steine thiolactone hydrochloride.

7. The reagent of claim 1, or 2, comprising at least about 40% v/v of a non-reactive aqueous component and an aqueous miscible polyol organic solvent in an amount of from about 45% to about 60% v/v, the solvent being a liquid at least at room temperature when dissolved in the aqueous component, the coenzyme therein being in an amount of from about 200 to about 400 mM, and the pH of the reagent is from about 1½ to about 2.

8. The reagent of claim 7, wherein the sulfhydryl compound is L-cysteine ethyl ester hydrochloride, in an amount of from about 60 to about 100 mM.

9. The reagent of claim 7, wherein the sulfhydryl compound is L-cysteine ethyl ester hydrochloride, and wherein the ratio of the concentration of NAD to the concentration of the sulfhydryl compound is from about 2 to about 6½:1.

10. The reagent of claim 7, wherein the sulfhydryl compound is N-Acetyl cysteine, in an amount of from about 80 to about 260 mM.

11. The reagent of claim 7, wherein the sulfhydryl compound is N-acetyl-cysteine, and wherein the ratio of the concentration of NAD to the concentration of the sulfhydryl compound is from ¾ to about 5:1.

12. The reagent of claim 7, wherein the sulfhydryl compound is DL-homocysteine thiolactone hydrochloride, in an amount of from about 170 to about 500 mM.

13. The reagent of claim 7, wherein the sulfhydryl compound is DL-homocysteine thiolactone hydrochloride, and wherein the ratio of the concentration of NAD to the concentration of the sulfhydryl compound is from ½ to about 2½:1.

14. The reagent of claim 7, wherein the NAD coenzyme is in an amount of about 330 mM, and wherein the sulfhydryl compound is L-cysteine ethyl ester hydrochloride in an amount of about 80 mM.

15. The reagent of claim 7, wherein the NAD coenzyme is in an amount of about 330 mM, and wherein the sulfhydryl compound is N-acetyl-cysteine in an amount of about 170 mM.

16. The reagent of claim 7, wherein the NAD coenzyme is in an amount of about 330 mM, and wherein the sulfhydryl compound is DL-homocysteine thiolactone hydrochloride in an amount of about 340 mM.

17. The reagent of claim 1, or 2, wherein the sulfhydryl compound is placed in solution in the NAD reagent less than about 1 day after the NAD coenzyme is placed in solution in the reagent.

18. The reagent of claim 1, or 2, wherein the sulfhydryl compound is placed in solution in the NAD reagent less than about 1 hour after the NAD coenzyme is placed in solution in the reagent.

19. The reagent of claim 1, or 2, wherein the sulfhydryl compound is placed in solution in the NAD reagent more than about 15 minutes before the reagent is used in a LD-L assay.

20. The NAD reagent of claim 1, wherein the sulfhydryl compound is placed in solution in the NAD reagent more than 1 hour before the reagent is used in a LD-L assay.

21. The NAD reagent of claim 1, wherein the sulfhydryl compound is placed in solution in the NAD reagent more than 1 day before the reagent is used in a LD-L assay.

22. A liquid NAD conenzyme reagent with an extended shelf life, the reagent for use for the quantitative determination of lactate dehydrogenase or lactate in a LD-L assay, the reagent comprising:
   (a) NAD coenzyme, in an amount of from about 200 to about 400 mM;

(b) at least about 40% v/v of a non-reactive aqueous component;

(c) an aqueous miscible polyol organic solvent in an amount of from about 45% to about 60% v/v; and (d) a sulfhydryl compound capable of counteracting the inhibitory effects of the degradation products of NAD on LD-L activity; the reagent having a pH of from about 1½ to about 2; the sulfhydryl compound being present in an amount sufficient so that when the reagent is stored in the substantial absence of oxygen at a temperature in the range of from about 2° to about 8° C., the reagent for a period of at least 2 years maintains a LD-L activity of at least about 90% of that of the reagent when the NAD coenzyme was first put in solution in the reagent; and wherein the sulfhydryl compound is placed in solution in the reagent more than about 15 minutes before the reagent is used in a LD-L assay.

23. The reagent of claim 22 wherein the sulfhydryl compound is selected from the group consisting of L-cysteine, Mercaptoethanol, Dithiothreitol, Dithioerythritol, Aminoethylisothiouronium bromide, Glutathione, Thioglycolic acid, N-Guanyl-L-cysteine, N-Guanyl-DL-isocyanate, N-Acetyl-S-guanyl-L-cysteine, N-Acetyl-S-benzyl-L-cysteine, N,S-Diguanyl-L-cysteine, S-Carbamoyl-L-cysteine, S-Carboxymethyl-L-cysteine, L-Thiazolidine-4-carboxylic acid, S-Guanyl-L-cysteinehydantoin, S-Acetylguanyl-DL-cysteineazlactone, 2-Imino-L-cysteinehydantoin, N-Acetyl-DL-homocysteinethiolactone, 1,3 Pimercapto-2-propanol, 2,3 Pimercapto-1-propanol, 1,2 Dimercapto-ethane, L-Cysteinemethyl ester, L-Cysteineethyl ester, N-Acetyl-DL-isocysteine, Polyethyleneglycol dimercaptoacetate, Thioglucose, Thioglycerol, L-cysteine ethyl ester hydrochloride, N-acetyl-cysteine, and DL-homocysteine thiolactone hydrochloride.

24. An analytical method for the quantitative determination of lactate dehydrogenase or lactate in a LD-L assay, comprising the step of mixing:

(a) a first solution containing the enzyme lactate dehydrogenase, (b) a second solution containing the substrate lactic acid or lactate; and (c) a third solution containing at least about 200 mM of NAD coenzyme, and a sulfhydryl compound capable of counteracting the inhibitory effects of the degradation products of the NAD coenzyme on LD-L activity, the third solution having a pH of less than about 3½, and the sulfhydryl compound being in a sufficient amount that when the third solution is stored in the substantial absence of oxygen at a temperature in the range of from about 2° to about 8° C., the third solution for a period of at least about 2 years maintains a LD-L activity of at least about 90% of that of the third solution when the NAD coenzyme was first put in solution in the third solution; to form a combined LD-L assay mixture.

25. The method of claim 24, wherein the second solution also contains a buffer, and the three solutions are mixed in such proportions that the assay mixture has a pH of about 8.5 to ±0.2.

26. The method of claim 24, wherein the sulfhydryl compound is selected from the group consisting of L-cysteine, Mercaptoethanol, Dithiothreitol, Dithioerythritol, Aminoethylisothiouronium bromide, Glutathione, Thioglycolic acid, N-Guanyl-L-cysteine, N-Guanyl-DL-isocyanate, N-Acetyl-S-guanyl-L-ysteine, N-Acetyl-S-benzyl-L-cysteine, N,S-Diguanyl-L-cysteine, S-Carbamoyl-L-cysteine, S-Carboxymethyl-L-cysteine, L-Thiazolidine-4-carboxylic acid, S-Guanyl-L-cysteinehydantoin, S-Acetylguanyl-DL-cysteineazlactone, 2-Imino-I-cysteinehydantoin, N-Acetyl-DL-homocysteinethiolactone, 1,3 Dimercapto-2-propanol, 2,3 Dimercapto-1-propanol, 1,2 Dimercapto-ethane, L-Cysteinemethyl ester, L-Cysteineethyl ester, N-Acetyl-DL-isocysteine, Polyethyleneglycol dimercaptoacetate, Thioglucose, Thioglycerol, L-cysteine ethyl ester hydrochloride, N-acetyl-cysteine, and DL-homocysteine thiolactone hydrochloride.

27. The method of claim 24, wherein the third solution comprises at least 40% of a non-reactive aqueous component and an aqueous miscible polyol organic solvent in an amount of from about 45% to about 60% v/v, the solvent being a liquid at least at room temperature when dissolved in the aqueous component, the coenzyme in the third solution being in an amount of from about 200 to about 400 mM, and the pH of the third solution being about 1½ to about 2.

28. The method of claim 27, wherein the sulfhydryl compound is L-cysteine ethyl ester hydrochloride, in an amount of from about 60 to about 100 mM.

29. The method of claim 27, wherein the sulfhydryl compound is L-cysteine ethyl ester hydrochloride, and wherein the ratio of the concentration of the coenzyme to the concentration of the sulfhydryl compound is from about 2 to about 6½:1.

30. The method of claim 27, wherein the sulfhydryl compound is N-Acetyl-cysteine, in an amount of from about 80 to about 260 mM.

31. The method of claim 27, wherein the sulfhydryl compound is N-acetyl-cysteine, and wherein the ratio of the concentration of the coenzyme to the concentration of the sulfhydryl compound is from about ¾ to about 5:1.

32. The method of claim 27, wherein the sulfhydryl compound is DL-homocysteine thiolactone, in an amount of from about 170 to about 500 mM.

33. The method of claim 27, wherein the sulfhydryl compound is DL-homocysteine thiolactone hydrochloride, and wherein the ratio of the concentration of the coenzyme to the concentration of the sulfhydryl compound is from about ½ to about 2½:1.

34. The method of claim 27, wherein the coenzyme is in an amount of about 330 mM, and wherein the sulfhydryl compound is L-cysteine ethyl ester hydrochloride in an amount of about 80 mM.

35. The method of claim 27, wherein the coenzyme is in an amount of about 330 mM, and wherein the sulfhydryl compound is N-acetyl-cysteine in an amount of about 170 mM.

36. The method of claim 27, wherein the coenzyme is in an amount of about 330 mM, and wherein the sulfhydryl compound is DL-homocysteine thiolactone hydrochloride in an amount of about 340 mM.

37. The method of claim 24, wherein the sulfhydryl compound is placed in solution in the third solution more than about 15 minutes before the third solution is used in the LD-L assay.

38. A method for preparing a liquid NAD coenzyme reagent with an extended shelf life, the reagent for use in the quantitative determination of lactate dehydrogenase or lactate in a LD-L assay, the method comprising the steps of:

(a) selecting components comprising:

(i) a non-reactive aqueous component;
(ii) an aqueous miscible polyol organic solvent, the solvent being a liquid at least at room temperature when dissolved in the aqueous component;
(iii) NAD coenzyme; and
(iv) a sulfhydryl compound capable of counteracting the inhibitory effects of the degradation products of NAD on LD-L activity;

(b) mixing the components to form the NAD reagent, the components being in such proportions that the aqueous component is in an amount of at least about 40% v/v, the solvent is in an amount of from about 45% to about 60% v/v; and (c) maintaining the pH of the NAD reagent at less than about 3½; the sulfhydryl compound being in a sufficient amount such that, when the reagent is stored in the substantial absence of oxygen at a temperature in the range of from about 2 to about 8° C., the reagent for a period of at least about 2 years maintains a LD-L activity of at least about 90% of that of the reagent when the NAD coenzyme was first put in solution in the reagent.

39. The method of claim 38, wherein the sulfhydryl compound is selected from the group consisting of L-cysteine, Mercaptoethanol, Dithiothreitol, Dithioerythritol, Aminoethylisothiouronium bromide, Glutathione, Thioglycolic acid, N-Guanyl-L-cysteine, N-Guanyl-DL-isocyanate, N-Acetyl-S-guanyl-L-cysteine, N-Acetyl-S-benzyl-L-cysteine, N,S-Diguanyl-L-cysteine, S-Carbamoyl-L-cysteine, S-Carboxymethyl-L-cysteine, L-Thiazolidine-4-carboxylic acid, S-Guanyl-L-cysteinehydantoin, S-Acetylguanyl-DL-cysteineazlactone, 2-Imino-L-cysteinehydantoin, N-Acetyl-DL homocysteinethiolactone, 1,3 Dimercapto-2-propanol, 2,3 Dimercapto-1-propanol, 1,2 Dimercapto-ethane, L-Cysteinemethyl ester, L-Cysteineethyl ester, N-Acetyl-DL-isocysteine, Polyethyleneglycol dimercaptoacetate, Thioglucose, and Thioglycerol.

40. The method of claim 38, wherein the sulfhydryl compound is L-cysteine ethyl ester hydrochloride.

41. The method of claim 38, wherein the sulfhydryl compound is N-acetyl-cysteine.

42. The method of claim 38, wherein the sulfhydryl compound is DL-homocysteine thiolactone.

43. The method of claim 38, wherein the polyol solvent is glycerol, in an amount of about 53% v/v, the coenzyme is in an amount of from about 200 to about 400 mM, and the pH of the reagent is from about 1½ to about 2.

44. The method of claim 38, wherein the sulfhydryl compound is L-cysteine ethyl ester hydrochloride, and wherein the ratio of the concentration of NAD coenzyme to the concentration of the sulfhydryl compound is from about 2 to about 6½:1.

45. The method of claim 43, wherein the sulfhydryl compound is N-acetyl-cysteine, and wherein the ratio of the concentraion of NAD to the concentration of the sulfhydryl compound is from about ¾ to about 5:1.

46. The method of claim 43, wherein the sulfhydryl compound is DL-homocysteine thiolactone hydrochloride, and wherein the ratio of the concentration of NAD coenzyme to the concentration of the sulfhydryl compound is from about ½ to about 2½:1.

47. The method of claim 39, wherein the sulfhydryl compound is placed in solution in the NAD reagent less than about 1 day after the NAD coenzyme is placed in solution in the reagent.

48. The method of claim 39, wherein the sulfhydryl compound is placed in solution in the NAD reagent more than about 15 minutes before the reagent is used in a LD-L assay.

49. A liquid NADP coenzyme reagent with an extended shelf life, the reagent for use for the quantitative determination of lactate dehydrogenase or lactate in a LD-L assay, the reagent comprising:
(a) NADP coenzyme, in an amount of from about 200 to about 400 mM;
(b) at least about 40% v/v of a non-reactive aqueous component;
(c) an aqueous miscible polyol organic solvent in an amount of from about 45% to about 60% v/v; and
(d) a sulfhydryl compound capable of counteracting the inhibitory effects of the degradation products of NADP on LD-L activity; the reagent having a pH of from about 1½ to about 2; the sulfhydryl compound being present in an amount sufficient so that when the reagent is stored in the substantial absence of oxygen at a temperature in the range of from about 2 to about 8° C., the reagent for a period at least 2 years maintains a LD-L activity of at least about 90% of that of the reagent when the NADP coenzyme was first put in solution in the reagent; and wherein the sulfhydryl compound is placed in the reagent more than about 15 minutes before the reagent is used in a LD-L assay.

50. An analytical method for the quantitative determination of lactate dehydrogenase or lactate in a LD-L assay, comprising the step of mixing:
(a) a first solution containing the enzyme lactate dehydrogenase,
(b) a second solution containing the substrate lactic acid or lactate; and
(c) a third solution containing at least about 200 mM of NADP coenzyme, and a sulfhydryl compound capable of counteracting the inhibitory effects of the degradation products of the NADP coenzyme on LD-L activity, the third solution having a pH of less than about 3½, and the sulfhydryl compound being in a sufficient amount that when the third solution is stored in the substantial absence of oxygen at a temperature in the range of from about 2° to about 8° C., the third solution for a period of at least about 2 years maintains a LD-L activity of at least about 90% of that of the third solution when the NADP coenzyme was first put in solution in the third solution; to form a combined LD-L assay mixture.

51. A method for preparing a liquid NADP coenzyme reagent with an extended shelf life, the reagent for use in the quantitative determination of lactate dehydrogenase or lactate in a LD-L assay, the method comprising the steps of:
(a) selecting components comprising:
(i) a non-reactive aqueous component;
(ii) an aqueous miscible polyol organic solvent, the solvent being a liquid at least at room temperature when dissolved in the aqueous component;
(iii) NADP coenzyme; and
(iv) a sulfhydryl compound capable of counteracting the inhibitory effects of the degradation products of NADP on LD-L activity;
(b) mixing the components to form the NADP reagent, the components being in such proportions that the aqueous component is in an amount of at least about 40% v/v, the solvent is in an amount of from about 45% to about 60% v/v; and (c) maintaining the pH of the NADP reagent at least than about 3½; the sulfhydryl compound being in a sufficient amount such that, when the reagent is stored in the substantial absence of oxygen at a temperature in the range of from about 2° to about 8° C., the reagent for a period of at least about two years maintains a LD-L activity of at least about 90% of that of the reagent when the NADP coenzyme was first put in solution in the reagent.

52. The NAD reagent of claim 1, comprising a non-reactive aqueous component and an aqueous miscible polyol organic solvent, the solvent being a liquid at least at room temperature when dissolved in the aqueous component.

53. The method of claim 24, wherein the third solution comprises a non-reactive aqueous component and an aqueous miscible polyol organic solvent, the solvent being a liquid at least at room temperature when dissolved in the aqueous component.

54. The NADP reagent of claim 2, comprising a non-reactive aqueous component and an aqueous miscible polyol organic solvent, the solvent being a liquid at least at room temperature when dissolved in the aqueous component.

55. The method of claim 25 wherein the third solution comprises a non-reactive aqueous component and an aqueous miscible polyol organic solvent, the solvent being a liquid at least at room temperature when dissolved in the aqueous component.

56. A liquid NAD coenzyme reagent with an extended shelf life, the reagent for use for the quantitative determination of lactate dehydrogenase or lactate in a LD-L assay, the reagent comprising NAD coenzyme, and a sulfhydryl compound capable of counteracting the inhibitory effects of the degradation products of NAD coenzyme on LD-L activity, the reagent having a pH of less than about 3½, and the sulfhydryl compound being in a sufficient amount that when the reagent is stored in the substantial absence of oxygen at a temperature of less than about 25° C., the reagent for a period of at least about 2 months maintains a LD-L activity of at least about 90% of that of the reagent when the coenzyme was first put in solution in the reagent.

57. A liquid NADP coenzyme reagent with an extended shelf life, the reagent for use for the quantitative determination of lactate dehydrogenase or lactate in a LD-L assay, the reagent comprising NADP coenzyme, and a sulfhydryl compound capable of counteracting the inhibitory effects of the degradation products of NADP coenzyme on LD-L activity, the reagent having a pH of less than about 3½, and the sulfhydryl compound being in a sufficient amount that when the reagent is stored in the substantial absence of oxygen at a temperature of less than about 25° C., the reagent for a period of at least about 2 months maintains a LD-L activity of at least about 90% of that of the reagent when the coenzyme was first put in solution in the reagent.

* * * * *